(12) United States Patent
Moriuchi et al.

(10) Patent No.: US 7,431,732 B2
(45) Date of Patent: Oct. 7, 2008

(54) STENT WITH WAVED CONNECTING MEMBERS

(75) Inventors: Yousuke Moriuchi, Fujinomiya (JP); Takashi Kitaoka, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 186 days.

(21) Appl. No.: 10/044,969

(22) Filed: Jan. 15, 2002

(65) Prior Publication Data

US 2002/0095207 A1 Jul. 18, 2002

(30) Foreign Application Priority Data

Jan. 15, 2001 (JP) ............... 2001-006759
Jun. 1, 2001 (JP) ............... 2001-166672

(51) Int. Cl.
*A61F 2/06* (2006.01)
(52) U.S. Cl. ............... 623/1.15; 623/1.16
(58) Field of Classification Search ............... 623/1.15, 623/1.16
See application file for complete search history.

(56) References Cited

U.S. PATENT DOCUMENTS

| | | | |
|---|---|---|---|
| 4,733,665 A | 3/1988 | Palmaz | |
| 4,739,762 A | 4/1988 | Palmaz | |
| 4,762,128 A | 8/1988 | Rosenbluth | |
| 4,886,062 A | 12/1989 | Wiktor | |
| 5,102,417 A | 4/1992 | Palmaz | |
| 5,195,984 A | 3/1993 | Schatz | |
| 5,421,955 A | 6/1995 | Lau et al. | |
| 5,449,373 A | 9/1995 | Pinchasik et al. | |
| 5,514,154 A * | 5/1996 | Lau et al. ............... | 623/1.15 |
| 5,569,295 A | 10/1996 | Lam | |
| 5,603,721 A | 2/1997 | Lau et al. | |

(Continued)

FOREIGN PATENT DOCUMENTS

EP 0 870 483 A2 10/1998

(Continued)

OTHER PUBLICATIONS

International Preliminary Examination Report issued in connection with corresponding international application, PCT/JP02/0048.

(Continued)

*Primary Examiner*—(Jackie) Tan-Uyen Ho
*Assistant Examiner*—Darwin P. Erezo
(74) *Attorney, Agent, or Firm*—Buchanan Ingersoll & Rooney PC

(57) ABSTRACT

A stent includes a plurality of annular expanding members arranged a predetermined distance apart from each other in the axial direction of the stent and each formed of a waved element, and a plurality of waved connecting members connecting the ridges and/or bottoms of the waved elements of adjacent annular expanding members. The plural annular expanding members are arranged in the axial direction of the stent such that no substantial phase difference exists between the waves of the waved element. Each waved connecting member has a plurality of waves including a wave positioned in the clearance between the adjacent annular expanding members and having an amplitude larger than that of the other wave. Also disclosed is a stent in which the expanding member is formed of a waved element arranged to surround spirally the longitudinal axis of the stent.

24 Claims, 6 Drawing Sheets

U.S. PATENT DOCUMENTS

| | | | |
|---|---|---|---|
| 5,643,312 A | 7/1997 | Fischell et al. | |
| 5,649,952 A | 7/1997 | Lam | |
| 5,697,971 A | 12/1997 | Fischell et al. | |
| 5,728,158 A | 3/1998 | Lau et al. | |
| 5,733,303 A | 3/1998 | Israel et al. | |
| 5,735,893 A | 4/1998 | Lau et al. | |
| 5,766,238 A | 6/1998 | Lau et al. | |
| 5,843,120 A | 12/1998 | Israel et al. | |
| 5,843,175 A | 12/1998 | Frantzen | |
| 5,876,449 A | 3/1999 | Starck et al. | |
| 5,879,370 A | 3/1999 | Fischell et al. | |
| 5,902,332 A | 5/1999 | Schatz | |
| 5,911,754 A | 6/1999 | Kanesaka et al. | |
| 5,913,895 A * | 6/1999 | Burpee et al. | 623/1.2 |
| 5,916,234 A | 6/1999 | Lam | |
| 5,922,021 A | 7/1999 | Jang | |
| 5,925,061 A | 7/1999 | Ogi et al. | |
| 5,954,743 A | 9/1999 | Jang | |
| 5,964,798 A | 10/1999 | Imran | |
| 5,972,018 A | 10/1999 | Israel et al. | |
| 5,980,552 A | 11/1999 | Pinchasik et al. | |
| 6,042,597 A | 3/2000 | Kveen et al. | |
| 6,056,776 A | 5/2000 | Lau et al. | |
| 6,059,811 A | 5/2000 | Pinchasik et al. | |
| 6,068,656 A | 5/2000 | Von Oepen | |
| 6,113,627 A * | 9/2000 | Jang | 623/1.5 |
| 6,183,506 B1 | 2/2001 | Penn et al. | |
| 6,190,403 B1 * | 2/2001 | Fischell et al. | 623/1.16 |
| 6,217,608 B1 * | 4/2001 | Penn et al. | 623/1.16 |
| 6,261,319 B1 * | 7/2001 | Kveen et al. | 623/1.15 |
| 6,352,552 B1 * | 3/2002 | Levinson et al. | 623/1.15 |
| 6,478,816 B1 * | 11/2002 | Kveen et al. | 623/1.15 |
| 6,616,689 B1 * | 9/2003 | Ainsworth et al. | 623/1.16 |
| 6,629,994 B2 * | 10/2003 | Gomez et al. | 623/1.15 |
| 6,896,697 B1 * | 5/2005 | Yip et al. | 623/1.15 |
| 6,929,660 B1 * | 8/2005 | Ainsworth et al. | 623/1.15 |
| 2001/0044649 A1 * | 11/2001 | Vallana et al. | 623/1.15 |
| 2004/0088044 A1 * | 5/2004 | Brown et al. | 623/1.16 |

FOREIGN PATENT DOCUMENTS

| | | |
|---|---|---|
| EP | 0 875 215 A1 | 11/1998 |
| EP | 0 878 174 A2 | 11/1998 |
| EP | 0 945 107 A2 | 9/1999 |
| EP | 1 066 804 A2 | 1/2001 |
| WO | 97/32543 A1 | 9/1997 |
| WO | 97/32544 A1 | 9/1997 |
| WO | 98/40035 A1 | 9/1998 |
| WO | 99/02105 A1 | 1/1999 |
| WO | WO 00/02502 A1 | 1/2000 |

OTHER PUBLICATIONS

Official Action issued in priority JP Patent Application No. 2001-006759, Jun. 10, 2008, JPO, Japan, and English-language translation thereof.

* cited by examiner

STENT WITH WAVED CONNECTING MEMBERS

CROSS-REFERENCE TO RELATED APPLICATIONS

This application is based upon and claims the benefit of priority from the prior Japanese Patent Applications No. 2001-006759, filed Jan. 15, 2001; and No. 2001-166672, filed Jun. 1, 2001, the entire contents of both of which are incorporated herein by reference.

BACKGROUND OF THE INVENTION

1. Field of the Invention

The present invention relates to a stent for indwelling within a living body, which is used for improving a stricture section or a obstruction section occurring in a tubular lumen such as a blood vessel, a bile duct, the trachea, the gullet, the urethra, and other internal organs, particularly, to a stent of a balloon expansion type.

2. Description of the Related Art

A stent is generally a tubular medical instrument used for treating various diseases and indwelled in a stricture section or an obstruction section of a tubular lumen within a living body such as a blood vessel for expanding the stricture section or the obstruction section so as to ensure an inner cavity therein.

The stents include stents of a balloon expansion type and stents of a self-expansion type. The balloon expansion type stent does not perform the self-expansion function unlike the self-expansion type stent. In the balloon expansion type stent, the stent is inserted into a desired position and, then, the balloon is expanded within the stent so as to permit the expanding force of the balloon to expand (plastically deform) the stent and bring the stent into contact with the inner surface of the desired position of the tubular lumen, thereby fixing the stent to the desired position.

In general, the stent is required to perform the delivery function and the re-stricture or restenosis preventing function as basic functions. The delivery function is the function where the stent is carried to a desired position within a tubular lumen. Naturally, the delivery function is a basic function, because it is impossible to retain or indwell the stent in the desired position unless the stent is carried to the desired position. The factors relating to the delivery function of the balloon expansion type stent include the stent diameter under the state that the stent is mounted on a balloon catheter and the close contacting of the balloon with the stent under the state that the stent is mounted on the balloon catheter. Particularly important is the flexibility of the stent under the state that the stent is mounted on the balloon catheter.

The stent is required to be flexible under the mounted state on the balloon catheter in order to allow the stent to be delivered along the guide wire retained in, particularly, the bent and meandering blood vessel. It is possible for a stent poor in the flexibility in the axial direction to be incapable of following the guide wire, resulting in failure to be delivered to the lesion portion. Particularly, the difficulty is rendered prominent when it comes to a long stent. Also, when the stent is passed through a bent and calcified lesion, it is possible for the stent to be caught by the calcified hard inner membrane so as not to be moved further. Particularly, when the stent is bent, a part of the strut protrudes toward the outside so as to abut against a hard lesion portion and, thus, to fail to move further. An additional problem takes place in clinical medicine in some cases. Specifically, when the stent is brought back into the guiding catheter because the stent is incapable of passing through the diseased portion, it is possible for a part of the stent to be caught by the tip of the guiding catheter, resulting in failure to recover the stent. It is also possible for the stent to be dropped from the balloon catheter.

On the other hand, the re-stricture preventing function represents the function of preventing a re-stricture in the portion where the stent is retained. The construction of the stent that permits suppressing the occurrence of a re-stricture has not yet been clarified sufficiently because the re-stricture generating mechanism has not yet been clarified sufficiently and because it is difficult to carry out the re-stricture comparison test by the stent since the types of the disease are complicated and diversified in clinical research. However, it is said that the re-stricture tends to occur easily in the edge of the stent when it comes to a stent poor in flexibility in the axial direction. It is considered reasonable to understand that the re-stricture tends to take place easily because stress is applied to the edge of the stent if the stent is poor in flexibility so as to stimulate the blood vessel. Naturally, it is considered reasonable to understand that the stent should desirably be flexible even after expanded and indwelled. However, a stent that does not have a free portion in general is hard in the axial direction, leading to a high re-stricture occurrence in the edge portion of the stent.

BRIEF SUMMARY OF THE INVENTION

An object of the present invention is to provide a stent flexible in the axial direction either before or after the expansion.

According to a first aspect of the present invention, there is provided a stent formed to be tubular as a whole, having a first outer diameter capable of insertion into a tubular lumen of a living body, and capable of expansion to have a second outer diameter larger than the first outer diameter when an expanding force directed outward in the radial direction is imparted within the stent, comprising a plurality of annular expanding members arranged a predetermined distance apart from each other in the axial direction of the stent and each formed of a waved element; and a plurality of waved connecting members connecting ridges and/or bottoms of the waved elements of the adjacent annular expanding members; wherein the plural annular expanding members are arranged in the axial direction of the stent such that no substantial phase difference exists in the waves of the waved element, and each of the waved connecting members has a plurality of waves including a wave formed in the clearance between adjacent annular expanding members and having an amplitude larger than that of the other wave.

According to a second aspect of the present invention, there is provided a stent formed to be tubular as a whole, having a first outer diameter capable of insertion into a tubular lumen of a living body, and capable of expansion to have a second outer diameter larger than the first outer diameter when an expanding force directed outward in the radial direction is imparted within the stent, comprising an expanding member formed of a waved element arranged to spirally surround the longitudinal axis of the stent; and a plurality of waved connecting members connecting ridges and/or bottoms of the waved elements of the expanding member; wherein the waved element has ridges and bottoms periodically appearing in a manner to cross the circumferential direction of the stent, and each of the waved connecting members has a plurality of waves including a wave formed in the clearance between adjacent waved elements in the axial direction of the stent and having an amplitude larger than that of the other wave.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention, and together with the general description given above and the detailed description of the embodiments given below, serve to explain the principles of the present invention.

DETAILED DESCRIPTION OF THE INVENTION

The present invention will now be described in detail with reference to the accompanying drawings.

The flexible stent of the present invention is formed to be tubular as a whole, has a first outer diameter capable of insertion into a tubular lumen of a living body, and capable of expansion to have a second outer diameter larger than the first outer diameter when an expanding force directed outward in the radial direction is imparted within the stent.

Figure 1:
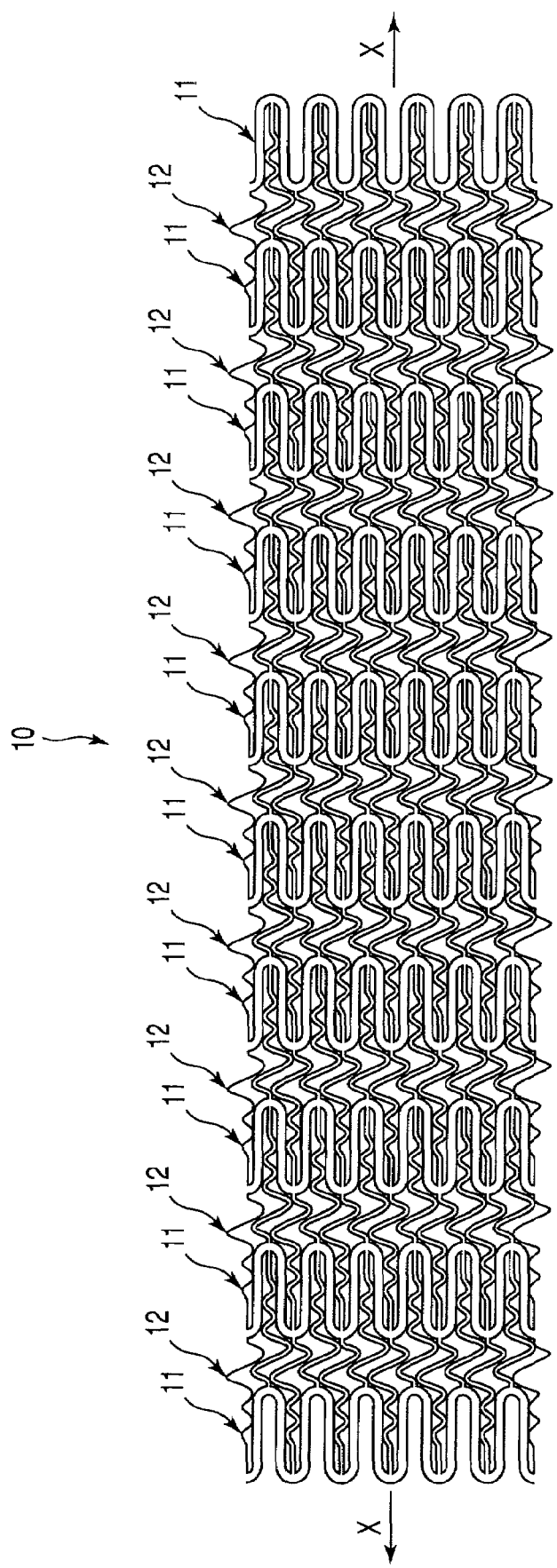
FIG. 1 is a magnified developed view before expansion of a stent according to a first embodiment of the present invention.
Figure 2:
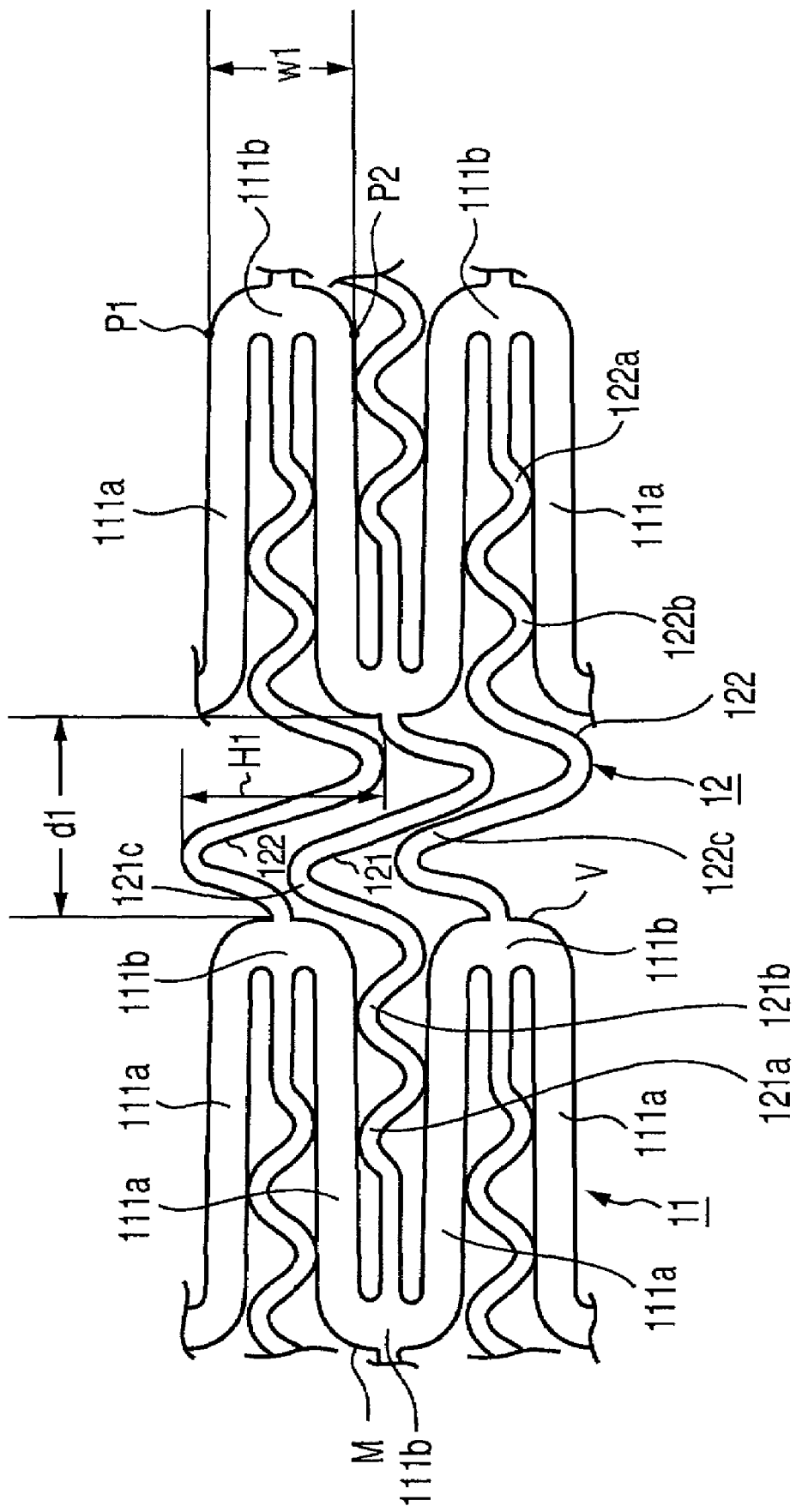
FIG. 2 is a developed view showing in a magnified fashion a part of the stent shown in FIG. 1.

FIG. 1 is a magnified developed view showing a stent 10 according to a first embodiment of the present invention under the state that the stent 10 is mounted on a balloon catheter, i.e., the state that the stent 10 has a first outer diameter small enough to permit the stent 10 to be inserted into a tubular lumen of a living body. FIG. 2 shows, in a magnified fashion, a part of the stent 10 shown in FIG. 1. Needless to say, the developed stent shown in FIG. 1 forms a tubular body if rolled around the longitudinal axis X.

The stent 10 shown in FIG. 1 comprises a plurality of annular expanding members 11, e.g., 10 annular expanding members 11, and a plurality of waved connecting members 12 each joining the adjacent annular expanding members 11. When an expanding force toward the outside in the radial direction is imparted inside each of the annular expanding members 11, the annular expanding member 11 is expanded to have a second outer diameter larger than the first outer diameter and, when the expanding force is removed, the annular expanding member 11 retains its expanded shape. Each of the annular expanding members 11 is formed of a waved element 111. Each of the waved elements 111 is formed in an annular fashion such that the ridges and the bottoms of the wave appear periodically in a manner to cross in the circumferential direction of the expanding member 11. It is desirable for all the waved elements 111 to have the same shape as shown in FIG. 1. As shown in FIG. 1, the annular expanding members 11 formed of the waved elements 111 are arranged parallel to each other with a predetermined distance d1 (see FIG. 2) provided therebetween in the longitudinal direction of the stent 10 denoted by arrows X in FIG. 1 such that no substantial phase difference of the wave is provided between the adjacent waved elements 111. In other words, the annular expanding members 11 are arranged such that the ridges of the adjacent annular expanding members 11 and the bottoms of the adjacent annular expanding members 11 are aligned in parallel in the axial direction of the stent 10. Incidentally, the bent portions on one side of the waved element 111 are defined to be the wave ridges, with the bent portions on the other side of the waved elements 111 being defined to be the wave bottoms. In this specification, the bent portions on the left side, which are denoted by M in FIG. 2, are defined to be the wave ridges, and the bent portions on the right side, which are denoted by V in FIG. 2, are defined to be the wave bottoms. In the embodiment shown in FIG. 1, each of the waved elements 111 has six ridges M and six bottoms V.

The wave form of the waved elements 111 constituting the annular expanding member 11 is not particularly limited. However, it is desirable for the wave form of the waved element 111 to be substantially U-shaped as shown in FIGS. 1 and 2. To be more specific, the U-shaped waved element 111 is formed of a substantially linear segment 111a and a bent segment 111b connected to the linear segment 111a, as shown in FIG. 2. The adjacent linear segments 111a are alternately connected to each other at the edge portions by a single bent segment 111b.

As clearly shown in FIG. 2, the waved connecting member 12 includes a wave ridge connecting element 12 for connecting the ridges of the waved elements 111 of the adjacent annular expanding members 11 and a wave bottom connecting element 122 for connecting the bottoms of the waved elements 111 of the adjacent annular expanding members 11. In the case of the stent shown in the drawing, the ridge connecting element 121 connects the ridge M on the left side to the ridge M on the right side. The ridge connecting element 121 has a plurality of, e.g., two, small waves 121a, 121b in the clearance between the adjacent linear segments 111a and a wave 121c having an amplitude larger than that of each of the other waves 121a, 121b in the clearance between the adjacent annular expansion members 11. Since the ridge connecting element 121 has the wave 121c having an amplitude larger than that of each of the other waves in the clearance between the adjacent annular expansion members 11, the flexibility of the stent 10 is increased. It is possible for the wave of the ridge connecting element to be V-shaped. However, it is desirable for the wave of the ridge connecting element to be S-shaped because the S-shaped wave causes directionality to be unlikely to appear when the stent 10 is bent. It is desirable for all the ridge connecting elements 121 to have the same shape. The ridge connecting element 121 shown in FIGS. 1 and 2 has two small waves in the clearance between the adjacent linear segments 111a and a single large wave in the clearance between the adjacent annular expanding members 11. However, the ridge connecting element 121 is not limited to the particular construction. It suffices for the ridge connecting element to have a plurality of waves including a wave formed between the adjacent annular expanding members and having an amplitude larger than that of each of the other waves.

The wave bottom connecting element 122 connects the bottom V of the wave on the left side to the bottom V of the wave on the right side. Like the ridge connecting element 121, the bottom connecting element 122 has a plurality of, e.g., two, small waves 122a, 122b in the clearance between the adjacent linear segments 111a and a wave 122c having an amplitude larger than that of each of the waves 122a, 122b between the adjacent annular expanding members 11. Since the bottom connecting element 122 has the wave 122c having an amplitude larger than that of each of the other waves in the clearance between the adjacent annular expanding members 11, the flexibility of the stent 10 is increased. It is desirable for the large wave 122c to have a wave height larger than the width of the clearance between the adjacent linear segments 111a. It is possible for the wave of the bottom connecting element 122 to be V-shaped. However, it is desirable for the wave of the bottom connecting element 122 to be S-shaped because the S-shaped wave causes the directionality to be unlikely to appear when the stent 10 is bent. It is desirable for all the bottom connecting elements 122 to have the same shape. The bottom connecting element 122 shown in FIGS. 1 and 2 has two small waves in the clearance between the adjacent linear segments 111a and a single large wave in the clearance between the adjacent annular expanding members 11. However, the bottom connecting element 122 is not limited to the particular construction. It suffices for the bottom connecting element to have a plurality of waves including a wave formed between the adjacent annular expanding members and having an amplitude larger than that of each of the other waves. In a particularly preferred embodiment of the present invention, all the ridge connecting elements 121 and all the bottom connecting members 122 have the same shape as shown in FIG. 1 and differ from each other in the direction alone. Also, it is desirable for all the ridges and all the bottoms of the waved elements constituting the adjacent expanding members 11 to be joined to each other by the connecting member 12.

In the present invention, in order to further increase the flexibility before and after the expansion, it is desirable for the large wave of the waved connecting member, i.e., the wave present in the clearance between the adjacent expanding members 12, to have a wave height H1 (see FIG. 2) larger than the width w1 of the ridge M or the bottom V of the waved element 111 constituting the annular expanding member 11. The width w1 of the ridge M or the bottom V represents the distance between points P1 and P2 at which one bent segment is brought into contact with the two linear segments 111a.

The annular expanding member 11 is required to be deformed when expanded and to retain the deformed state and, thus, is required to exhibit a coping force large enough to cope with the force generated when the blood vessel is shrunk. Therefore, it is desirable for the annular expanding member 11 to have a width and a thickness not smaller than predetermined levels. On the other hand, if the connecting member 12 is assumed to play simply the role of maintaining a predetermined distance between the adjacent annular expanding members 11, it is possible for the connecting member 12 to have a considerably small width. However, if the connecting member 12 is also allowed to play the role of expanding and holding the blood vessel, it is necessary for the connecting member 12 to have a width and a thickness substantially equal to those of the expanding member. As a result, the stent is rendered relatively poor in flexibility, though the stent exhibits a high expansion holding force.

However, the present invention is intended to provide a stent high in flexibility in the axial direction both before and after the expansion. As a result of extensive research, the present inventors have found that the flexibility can be further increased if the width of the connecting member 12 (the ridge connecting element 121 and the bottom connecting element 122) is set at a level not larger than ½ the width of the waved element 111 constituting the annular expanding member 11.

It has also been found that the stent function can be exhibited sufficiently, if the distance between the adjacent annular expanding members 11 is kept constant. To be more specific, it has been found that the width of the connecting member 12 should fall within a range of between 0.03 mm and 0.08 mm, more desirably between 0.04 mm and 0.06 mm.

If the distance d1 between the adjacent annular expanding members 11 is excessively large, the number per unit length of the expanding members 11 having the function of holding the expansion is decreased so as to relatively lower the expansion holding force, though it is certainly possible to increase the flexibility of the stent 10. On the other hand, if the distance d1 between the adjacent expanding members 11 is excessively small, the number of expanding members 11 per unit length is increased so as to relatively increase the expansion holding force. However, the flexibility is rendered relatively poor. As a result of extensive research into the measures to achieve a good balance between the conflicting demands of expansion holding and the flexibility, the present inventors have found that the distance d1 between the adjacent annular expanding members 11 should fall within a range of between 0.4 mm and 0.8 mm, more desirably between 0.5 mm and 0.7 mm.

Figure 3:
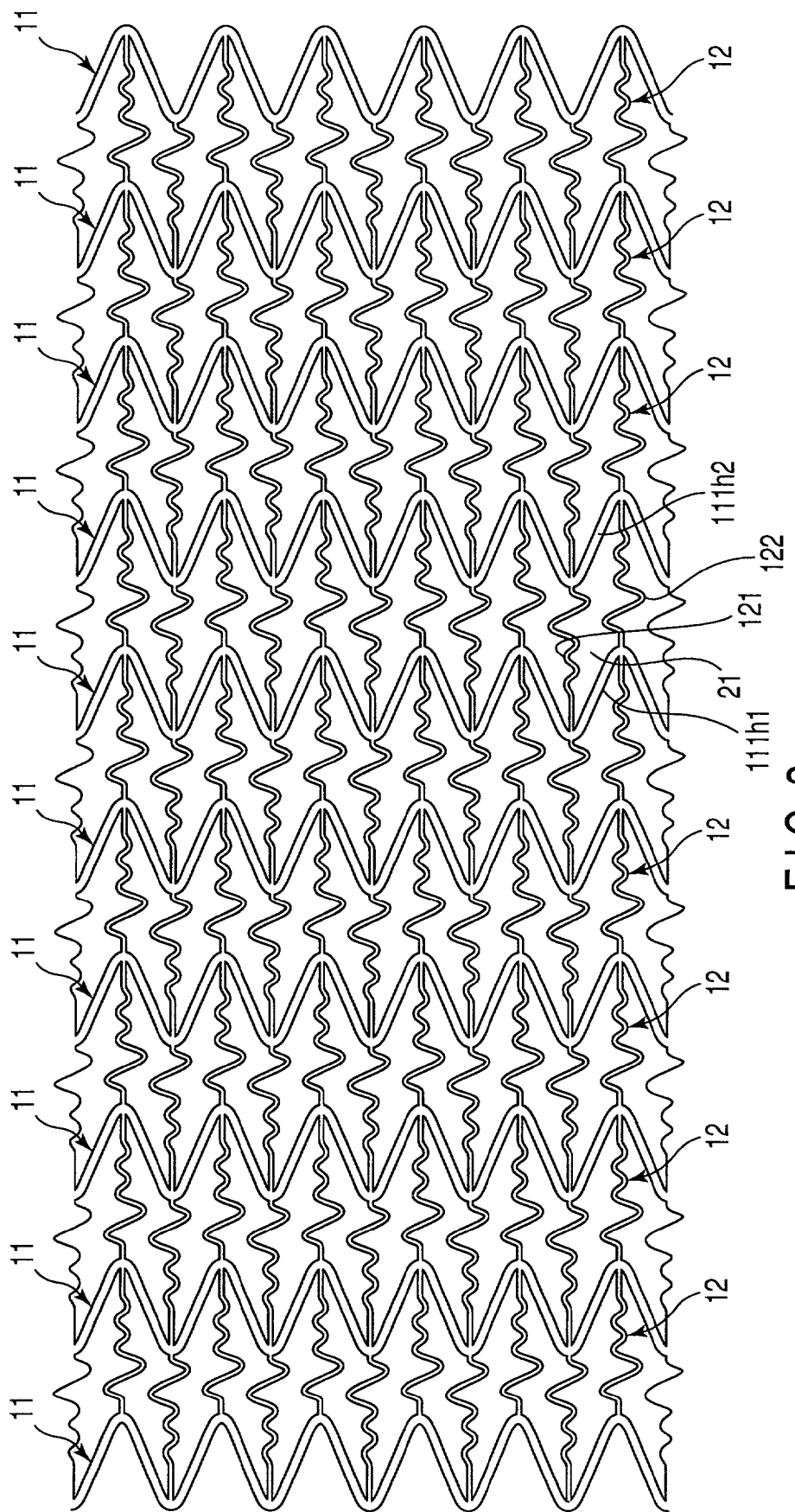
FIG. 3 is a developed view after expansion of the stent shown in FIG. 1.

FIG. 3 is a developed view showing the state that the stent 10 shown in FIG. 1 is expanded to have the second outer diameter referred to previously. As shown in the drawing, the waved element 111 constituting the annular expanding member 11 is deformed from the U-shape in the non-expansion step shown in FIG. 1 into a V-shape. In accordance with the deformation, the diameter of the stent 10 is increased. However, if the stent 10 is expanded within a linear blood vessel, which is not bent, the connecting member 12 is not basically changed in its shape and length. To be more specific, the length in the axial direction of the expanding member 11 is changed if the stent is expanded. However, the length of the connecting member 12 is not changed because the adjacent ridges or the adjacent bottoms of the connecting member 12 are changed in the same direction by the same length. On the other hand, if the wave of the waved element 111 of the expanding member 11 differs in phase by 180°, i.e., if the ridge and the bottom of the wave of the waved element 111 are connected, the distance between the adjacent expanding members 11 is increased in the expanding process so as to elongate the connecting member 12. In the stent of the present invention, the expanding members 11 are arranged in the axial direction such that there is no phase difference among the waves of the waved element 111 so as to produce the merit that the entire length is unlikely to be changed (not substantially changed) even if the stent is extremely expanded. If the entire length of the stent is decreased by the expansion, it is impossible to expand the entire region of the aimed stricture portion of a blood vessel, or there is a deviation between the arranging position assumed by the X-ray image formation and the actual arranging state of the stent, resulting in failure to improve effectively the stricture portion.

It should also be noted that, if the connecting member 12 is waved, it is possible to increase the flexibility of the stent as described previously. In addition, it is possible to obtain the merit that the treatment can be applied easily to a branched blood vessel. Particularly, the merit is prominent in the stent retained in the coronary artery. The coronary artery includes a main thick blood vessel, hereinafter referred to as a main blood vessel, and various branched blood vessels, i.e., thin blood vessels branched from the main blood vessel. Where the stricture is formed in the branched portion between the main blood vessel and the branched blood vessels, the stent is retained in some cases to extend into the branched portion.

Since the stent is retained, it is possible for the degree of stricture in the branched blood vessels to be increased or for the branched blood vessels to be closed in the portion of the stricture. In many cases, clinical symptoms or myocardial infarction do not take place because the branched blood vessels are thin. However, a chest pain or an infarction symptom is exhibited in some cases so as to make it necessary to apply some treatment.

In this case, the guide wire is inserted into a branched blood vessel through a clearance 21 of the stent shown in FIG. 3, and a balloon catheter is delivered into the stricture portion along the guide wire so as to expand and treat the stricture portion. In many cases, the stricture portion is present in the inlet of the branched blood vessel and, thus, the wall of the stent is also expanded. Also, in order to obtain a sufficient effect of the expansion, it is necessary to perform the expansion by using a large balloon having a diameter close to the diameter of the branched blood vessel. If the balloon is expanded, a half portion 111$h$ of the waved element 111 defining the clearance 21 of the stent, the ridge connecting element 121 and the bottom connecting element 122 which are adjacent to each other in the circumferential direction, and a half portion 111$h$2 of the waved element 111 adjacent to the half portion 111$h$1 of the waved element 111 are expanded into substantially circular form. As described above, it is desirable to perform the expansion with a balloon that is as large as possible and, thus, it is desirable for the circumferential length to be as large as possible. In the present invention, the connecting member 12 is waved and, thus, the circumferential length of the clearance 21 is larger than that in the case where the connecting member 12 is straight, leading to the merit that it is possible to use a large balloon. Such being the situation, it is particularly desirable for the total length of each of the waved connecting member 12 to be at least 1.3 times as much as the straight distance between the adjacent ridges or between the adjacent bottoms of the annular expanding member 11.

Figure 4:
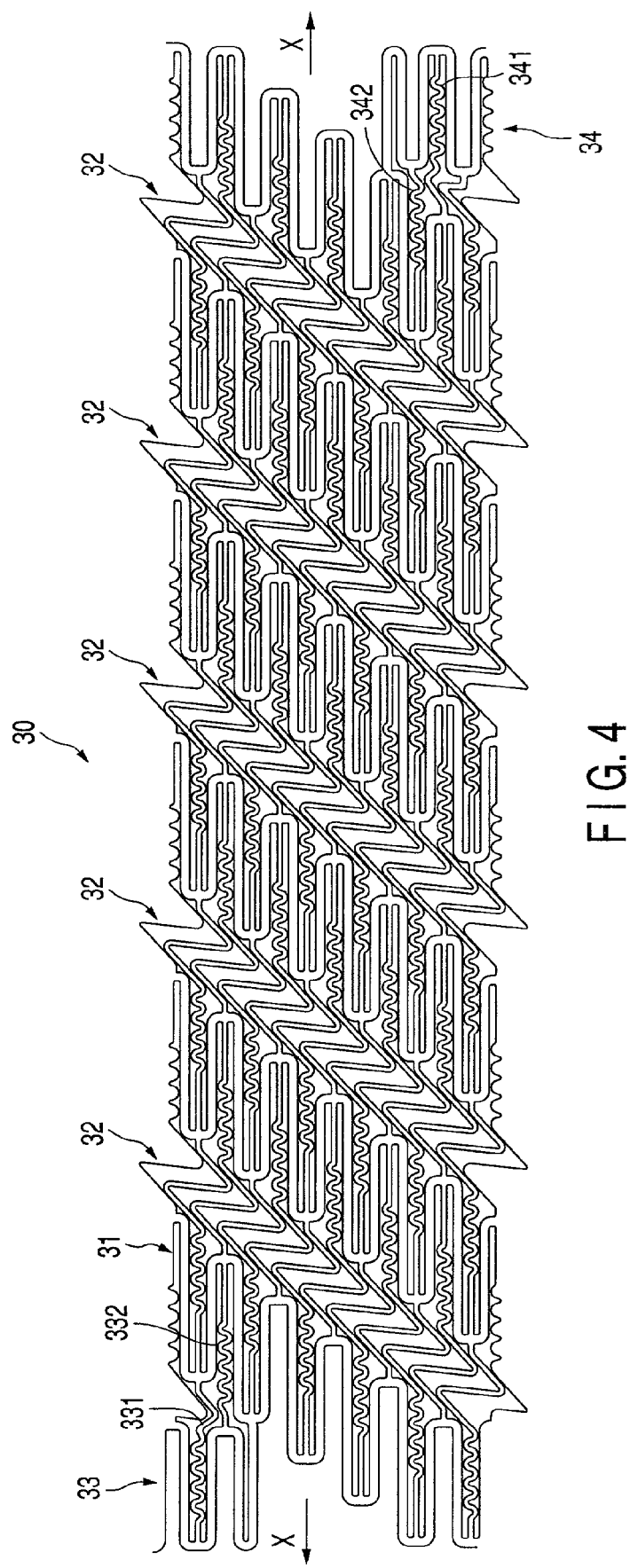
FIG. 4 is a magnified developed view before expansion of a stent according to a second embodiment of the present invention.
Figure 5:
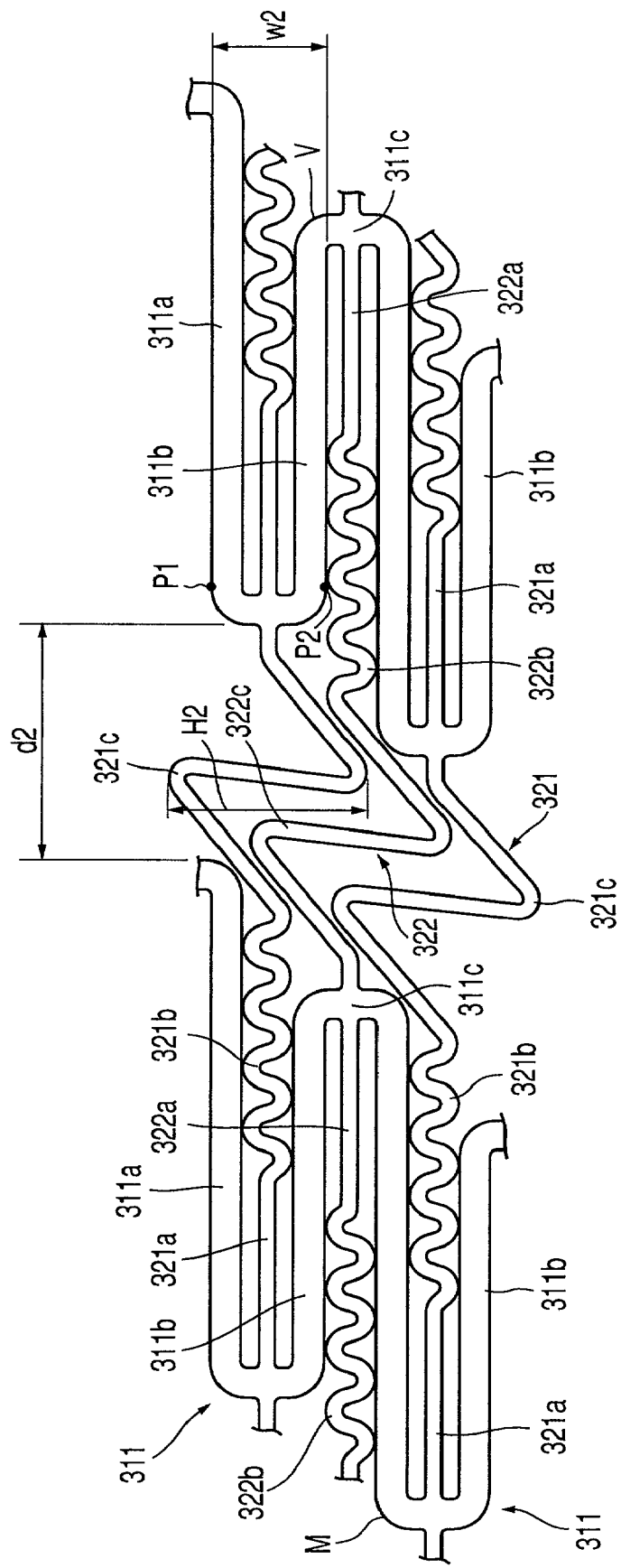
FIG. 5 is a developed view showing in a magnified fashion a part of the stent shown in FIG. 4.

FIG. 4 is a magnified developed view of a stent 30 according to the first mode of the present invention under the state that the stent 30 according to a second embodiment of the present invention is mounted on a balloon catheter, i.e., under the state that the stent has the first outer diameter that is small enough to be inserted into the tubular lumen of a living body. FIG. 5 shows in a magnified fashion a part of the stent 30 shown in FIG. 4. Needless to say, the developed stent shown in FIG. 4 forms a tubular body if rolled around the longitudinal axis X.

The stent 30 shown in FIGS. 4 and 5 comprises expanding members 31 formed of waved elements 311 and waved connecting members 32 for connecting the adjacent ridges and/or the adjacent bottoms of the waved element in the longitudinal axial direction of the stent denoted by arrows X.

When an expanding force toward the outside in the radial direction is imparted within the expanding member 31, the expanding member 31 is expanded to have a second outer diameter larger than the first outer diameter and retains the expanded shape when the expanding force is removed. The expanding member 31 performing the particular function is formed of a waved element 311 spirally arranged to surround the longitudinal axis of the stent.

The waved element 311 is formed in a spiral fashion such that the ridges and the bottoms of the wave periodically appear in the crossing direction with a predetermined angle relative to the circumferential direction of the expanding member 31.

It is desirable for the waved elements 311 to be arranged in the longitudinal axial direction of the stent 30 in parallel at a predetermined distance d2 (see FIG. 5) apart from each other such that no substantial phase difference is generated between the adjacent waves in the longitudinal axial direction of the stent. In other words, it is desirable for the expanding members 31 to be arranged such that the adjacent wave ridges and the adjacent wave bottoms in the longitudinal axial direction of the stent are aligned in parallel. Incidentally, the bent portion on one side of the waved element 311 is defined in the present specification to be the ridge of the wave, and the bent portion on the other side of the waved element 311 is defined to be the bottom of the wave. In FIGS. 4 and 5, the bent portion on the left side is defined to be the ridge of the wave, which is denoted by M in FIG. 5, and the bent portion on the right side is defined to be the bottom of the wave, which is denoted by V in FIG. 5. In the embodiment shown in FIG. 4, the waved element 311 makes a spiral rotation about six times.

The wave form of the waved element 311 constituting the expanding member 31 is not particularly limited in the present invention. However, it is desirable for the wave form to be substantially U-shaped as shown in FIGS. 4 and 5. To be more specific, the U-shaped waved element 311 comprises a substantially linear long segment 311$a$, a substantially linear short segment 311$b$, and a bent segment 311$c$ connecting these linear segments 311$a$ and 311$b$, as shown in FIG. 5. The adjacent linear long and short segments 311$a$ and 311$b$ are alternately connected to each other at the edge portions by a single bent segment 311$c$.

As clearly shown in FIG. 5, the waved connecting member 32 includes a wave ridge connecting element 321 connecting the adjacent wave ridges of the waved element 311 of the expanding member 31 in the axial direction of the stent and a wave bottom connecting element 322 connecting the adjacent wave bottoms of the waved element 311 of the expanding member 31 in the axial direction of the stent. In the case of the stent shown in the drawing, the ridge connecting element 321 connects the ridge M on the left side to the ridge M on the right side. The ridge connecting element 321 includes a plurality of, e.g., four, small waves 321$b$ formed in the clearance between the adjacent linear long segment 311$a$ and the short segment 311$b$ and a large wave 321$c$ having an amplitude larger than that of the other wave 321$b$, said large wave 321$c$ being formed in the clearance between the adjacent waved elements in the longitudinal axial direction of the stent. Since the large wave 321$c$ having an amplitude larger than that of the other wave is formed in the clearance between the adjacent waved elements 311, it is possible to increase the flexibility of the stent 30. Incidentally, in the stent shown in the drawing, the small wave 321$b$ is connected to a linear member 321$a$ connected to the ridge of the wave. It is possible for the wave of the ridge connecting element to be V-shaped. However, it is desirable for the wave of the ridge connecting element to be S-shaped because the S-shaped wave causes directionality to be unlikely to appear when the stent 10 is bent. It is desirable for all the ridge connecting elements 321 to have the same shape. The ridge connecting element 321 shown in FIGS. 4 and 5 has four small waves in the clearance between the adjacent linear long segment 311$a$ and the short segment 311$b$ and a single large wave 321$c$ in the clearance between the adjacent waved elements in the longitudinal axial direction of the stent. However, the ridge connecting element 321 is not limited to the particular construction. It suffices for the ridge connecting element to have a plurality of waves including a wave formed between the adjacent waved elements in the longitudinal axial direction of the stent and having an amplitude larger than that of each of the other waves.

The wave bottom connecting element 322 connects the bottom V of the wave on the left side to the bottom V of the wave on the right side. Like the ridge connecting element 321, the bottom connecting element 322 has a plurality of, e.g., four, small waves 322b in the clearance between the adjacent long linear segment 311a and the short linear segment 311b and a wave 322c having an amplitude larger than that of each of the waves 322b between the adjacent waved elements in the longitudinal axial direction of the stent. Since the bottom connecting element 322 has the wave 322c having an amplitude larger than that of each of the other waves in the clearance between the adjacent annular expanding members 11, the flexibility of the stent 30 is increased. It is desirable for the large wave 322c to have a wave height larger than the width of the clearance between the adjacent linear segments 311a. It is possible for the wave of the bottom connecting element 322 to be V-shaped. However, it is desirable for the wave of the bottom connecting element 322 to be S-shaped because the S-shaped wave causes directionality to be unlikely to appear when the stent 30 is bent. It is desirable for all the bottom connecting elements 322 to have the same shape. The bottom connecting element 322 shown in FIGS. 4 and 5 has four small waves 322b in the clearance between the adjacent long linear segments 311a and the short linear segment 311b and a single large wave 322c in the clearance between the adjacent waved elements in the longitudinal axial direction of the stent. However, the bottom connecting element 322 is not limited to the particular construction. It suffices for the bottom connecting element 322 to have a plurality of waves including a wave formed between the adjacent waved elements in the longitudinal axial direction of the stent and having an amplitude larger than that of each of the other waves. In a particularly preferred embodiment of the present invention, all the ridge connecting elements 321 and all the bottom connecting members 322 have the same shape as shown in FIG. 4 and differ from each other in the direction alone. Also, it is desirable for all the ridges and all the bottoms of the adjacent waved elements in the longitudinal axial direction of the stent to be joined to each other by the connecting member 32.

In the present invention, in order to further increase the flexibility before and after the expansion, it is desirable for the large wave of the waved connecting member, i.e., the wave present in the clearance between the adjacent expanding members 31, to have a wave height H2 (see FIG. 5) larger than the width w2 of the ridge M or the bottom V of the waved element 311 constituting the annular expanding member 31. The width w2 of the ridge M or the bottom V represents the distance between points P1 and P2 at which one bent segment is connected to the linear long segment 311a and the linear short segment 311b under the developed state of the stent.

The annular expanding member 31 is required to be deformed when expanded and to retain the deformed state and, thus, is required to exhibit a coping force large enough to cope with the force generated when the blood vessel is shrunk. Therefore, it is desirable for the annular expanding member 31 to have a width and a thickness not smaller than predetermined levels. On the other hand, if the connecting member 32 is assumed to play simply the role of maintaining a predetermined distance between the adjacent annular expanding members 31, it is possible for the connecting member 32 to have a considerably small width. However, if the connecting member 32 is also allowed to play the role of expanding and holding the blood vessel, it is necessary for the connecting member 32 to have a width and a thickness substantially equal to those of the expanding member. As a result, the stent is rendered relatively poor in flexibility, though the stent exhibits a high expansion holding force.

However, the present invention is intended to provide a stent high in flexibility in the axial direction both before and after the expansion. As a result of extensive research, the present inventors have found that the flexibility can be further increased if the width of the connecting member 32 (the ridge connecting element 321 and the bottom connecting element 322) is set at a level not larger than ½ the width of the waved element 311 constituting the annular expanding member 31. It has also been found that the stent function can be exhibited sufficiently if the distance between the adjacent annular expanding members 31 is kept constant. To be more specific, it has been found that the width of the connecting member 32 should fall within a range of between 0.03 mm and 0.08 mm, more desirably between 0.04 mm and 0.06 mm.

If the distance d2 between the adjacent waved elements 311 is excessively large, the number per unit length of the expanding members 31 having the function of holding the expansion is decreased so as to relatively lower the expansion holding force, though it is certainly possible to increase the flexibility of the stent 30. On the other hand, if the distance d2 between the adjacent expanding members 31 is excessively small, the number of expanding members 31 per unit length is increased so as to relatively increase the expansion holding force. However, the flexibility is rendered relatively poor. As a result of extensive research into the measures to achieve a good balance between the conflicting demands of expansion holding and the flexibility, the present inventors have found that the distance d2 between the adjacent annular expanding members 31 should fall within a range of between 0.4 mm and 1.7 mm, more desirably between 0.6 mm and 1.2 mm.

FIG. 4 shows that the stent 30 has a second waved element 33 and a third waved element 34 on both edges. The second and third waved elements 33 and 34 permit the tip of the wave form positioned on both edges under the state that the waved element 311 is arranged in a spiral fashion to be flush with both edges in a direction perpendicular to the longitudinal axis of the stent. The second waved element 33 is formed of two waves and is connected to the ridge of the wave at one edge portion. Also, the bottoms of the adjacent spiral waved element are connected to each other by the waved connecting member 331 and the ridges of the adjacent spiral waved element are connected to each other by the waved connecting member 332. On the other hand, the third waved element 34 is formed of two waves and is connected to the ridge of the wave at one edge portion. Also, the bottoms of the adjacent spiral waved element are connected to each other by the waved connecting member 341 and the ridges of the adjacent spiral waved element are connected to each other by the waved connecting member 342. Each of the connecting members 331, 332, 341 and 342 does not have a large wave as in the connecting member 32 for connecting the spiral waved element 311. However, no particular problem is generated because the flexibility is scarcely required in these connecting members 331, 332, 341 and 342.

Figure 6:
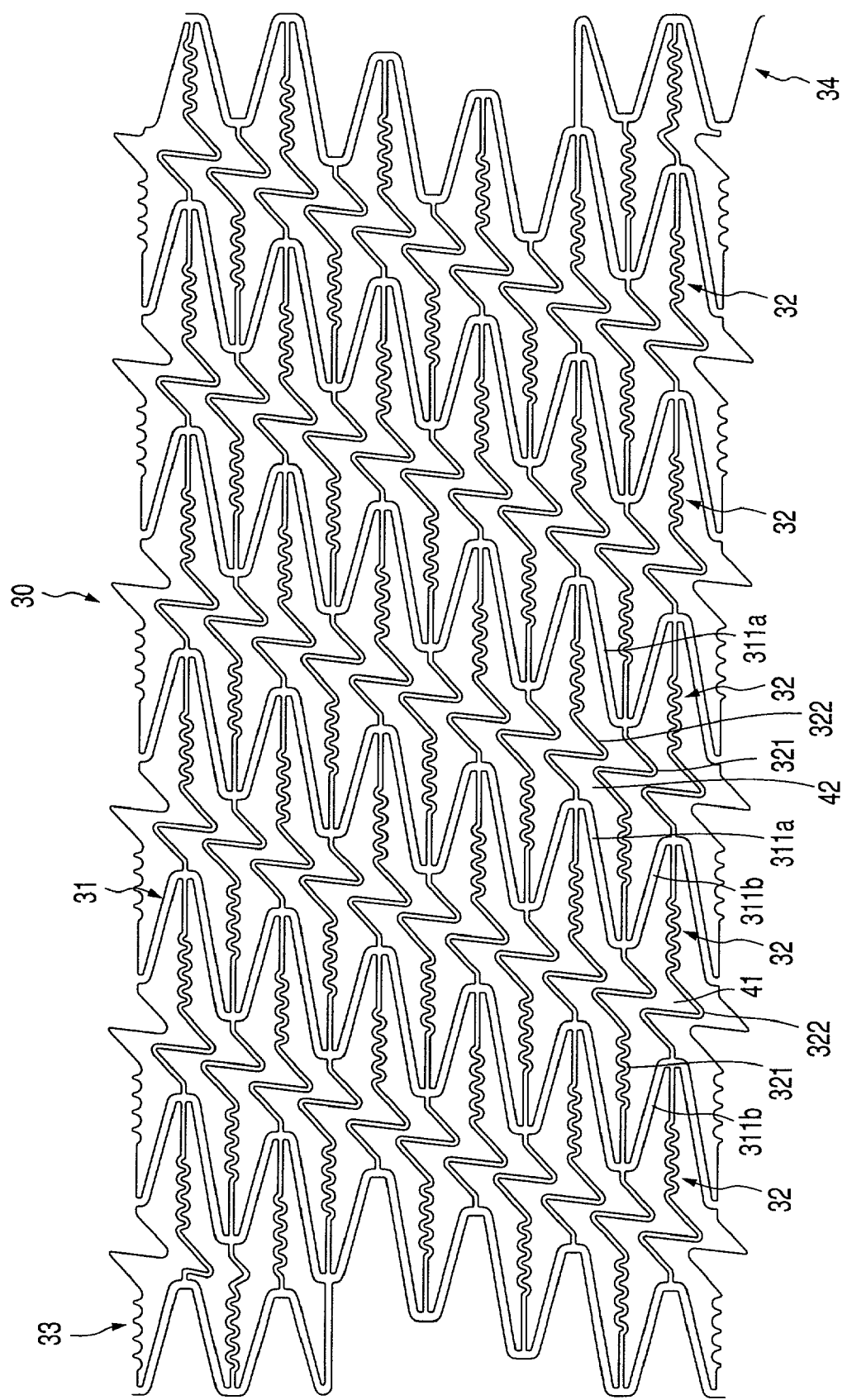
FIG. 6 is a developed view after expansion of the stent shown in FIG. 4.

FIG. 6 is a developed view showing the state that the stent 30 shown in FIG. 4 is expanded to have the second outer diameter referred to previously. As shown in the drawing, the waved element 311 constituting the annular expanding member 11 is deformed from the U-shape in the non-expansion step shown in FIG. 4 into a V-shape. In accordance with the deformation, the diameter of the stent 30 is increased. However, if the stent 30 is expanded within a linear blood vessel, which is not bent, the connecting member 32 is not basically changed in its shape and length. To be more specific, the length in the axial direction of the expanding member 31 is changed if the stent is expanded. However, the length of the connecting member 32 is not changed because the adjacent ridges or the adjacent bottoms of the connecting member 32 are changed in the same direction by the same length. On the other hand, if the wave of the waved element 311 of the expanding member 31 differs in phase by 180°, i.e., if the ridge and the bottom of the wave of the waved element 311 are connected, the distance between the adjacent expanding members 31 is increased in the expanding process so as to elongate the connecting member 32. In the stent of the present invention, the expanding members 31 are arranged in the axial direction such that there is no phase difference among the waves of the waved element 311 so as to produce the merit that the entire length is unlikely to be changed (not substantially changed) even if the stent is extremely expanded. If the entire length of the stent is decreased by the expansion, it is impossible to expand the entire region of the aimed stricture portion of a blood vessel, or there is a deviation between the arranging position assumed by the X-ray image formation and the actual arranging state of the stent, resulting in failure to improve effectively the stricture portion.

It should also be noted that, if the connecting member 32 is waved, it is possible to increase the flexibility of the stent as described previously. In addition, it is possible to obtain the merit that the treatment can be applied easily to a branched blood vessel. Particularly, the merit is prominent in the stent retained in the coronary artery. The coronary artery includes a main thick blood vessel, hereinafter referred to as a main blood vessel, and various branched blood vessels, i.e., thin blood vessels branched from the main blood vessel. Where the stricture is formed in the branched portion between the main blood vessel and the branched blood vessels, the stent is retained in some cases to extend into the branched portion. Since the stent is retained, it is possible for the degree of stricture in the branched blood vessels to be increased or for the branched blood vessels to be closed in the portion of the stricture. In many cases, clinical symptoms or myocardial infarction do not take place because the branched blood vessels are thin. However, a chest pain or an infarction symptom is exhibited in some cases so as to make it necessary to apply some treatment.

In this case, the guide wire is inserted into a branched blood vessel through a clearance 41 of the stent shown in FIG. 6, and a balloon catheter is delivered into the stricture portion along the guide wire so as to expand and treat the stricture portion. In many cases, the stricture portion is present in the inlet of the branched blood vessel and, thus, the wall of the stent is also expanded. Also, in order to obtain a sufficient effect of the expansion, it is necessary to perform the expansion by using a large balloon having a diameter close to the diameter of the branched blood vessel. If the balloon is expanded, the linear short segment 311b of the waved element 311 defining the clearance 41 of the stent, the ridge connecting element 321 and the bottom connecting element 322 which are adjacent to each other in the circumferential direction, and the short segment 311b of the waved element 311 adjacent to the short segment 311b of the waved element 311 in the axial direction are expanded into substantially circular form. As described above, it is desirable to perform the expansion with a balloon that is as large as possible and, thus, it is desirable for the circumferential length to be as large as possible. In the present invention, the connecting member 12 is waved and, thus, the circumferential length of the clearance 41 is larger than that in the case where the connecting member 32 is straight, leading to the merit that it is possible to use a large balloon. Such being the situation, it is particularly desirable for the total length of each of the waved connecting member 32 to be at least 1.3 times as much as the straight distance between the adjacent ridges or between the adjacent bottoms of the annu-lar expanding member 31. Incidentally, a large clearance 42 larger than the clearance 41 noted above is formed by the linear long segment 311a of the waved element 311, the ridge connecting element 321 and the bottom connecting element 322 adjacent to each other in the circumferential direction, and the long segment 311a of the waved element 311 adjacent to the long segment 311a of the waved element 311 in the axial direction. It is unclear, however, whether the guide wire actually passes through the clearance 41 or the clearance 42. Therefore, it is convenient to use a balloon capable of being inserted into the small clearance 41.

It is desirable for each of the stents 10 and 30 to be formed of a material adaptable to a living body including, for example, a stainless steel, tantalum or a tantalum alloy, platinum or a platinum alloy, gold or a gold alloy, and a cobalt-based alloy. It is also possible to prepare first a stent form, followed by plating the stent form with a noble metal such as gold or platinum. It is desirable to use as the stainless steel SUS316L having the highest corrosion resistance. Further, it is desirable to apply annealing to the final shape of the stent 10 after formation of the final shape of the stent 10. If annealing is applied, the flexibility and the plasticity of the entire stent are improved so as to improve the capability of being retained in a bent blood vessel. Compared with the case where annealing is not applied, a stent to which annealing is applied permits decreasing the restoring force of the expanded stent to the shape before the expansion, particularly, the restoring force to the linear state, which is exhibited when the stent is expanded in a bent portion of a blood vessel, so as to decrease the physical stimulus imparted to the inner wall of the bent blood vessel and, thus, to decrease the factor of the re-stricture. In order to prevent an oxide film from being formed on the surface of the stent, it is desirable to carry out the annealing by heating at 1000 to 1150° C. in an inert gas atmosphere, e.g., in an argon gas atmosphere, followed by rapidly cooling the stent.

Each of the stents 10 and 30 of the present invention can be manufactured preferably by employing the method of hollowing out the stent portion from a metal pipe. Various methods can be employed for hollowing out the stent from a pipe including, for example, an etching method called photo fabrication using masking and chemicals, a discharge processing method using a mold, and a mechanical cutting method.

The simplest method having a high processing accuracy is a laser processing method. It is possible to use SL116E (trade name of a YAG laser manufactured by NEC Corporation) as the laser processing machine. Specifically, a metal pipe is set on a tool equipped with a rotary motor provided with a chuck mechanism so as to prevent the axis of the metal pipe from being shifted, and the tool is set on an XY table capable of a numerical control. The XY table and the rotary motor are connected to a personal computer, and the output of the personal computer is set to be supplied to the numerical controller of the XY table and to the rotary motor. Drawing software is stored in the personal computer, and the developed drawing of the stent constructed as shown in FIG. 1 or 4 is supplied to the personal computer. Then, the XY table and the rotary motor are driven on the basis of the drawing data generated from the personal computer, followed by irradiation with a laser beam so as to prepare the stent structure shaped as shown in FIG. 1. The method of manufacturing the stent is not limited to the system described above. It is also possible to employ a so-called "laser marker" system (galvanometer system) driven by a laser processing machine.

A retaining technology of a coronary artery stent will now be described briefly as a typical stent retaining technology in the case of using a balloon expansion stent. In the first step, a sheath is retained in a suitable blood vessel (mainly a femoral artery, an elbow artery or the radial artery) in order to secure blood vessels for introducing various catheters into the blood vessels. The sheath is a device comprising a plastic tube having a small wall thickness and a valve mounted on the distal end of the plastic tube for preventing the leakage of the blood. Catheters can be inserted into and withdrawn from the plastic tube through the valve mounted at the distal end of the plastic tube. A catheter called a guiding catheter is inserted through the sheath so as to fix the distal end of the inserted catheter at the inlet of the right or left coronary artery. As a result, a passageway is formed extending from outside the living body to the coronary artery.

In the next step, a thin guide wire having a diameter of, for example, about 0.36 mm (0.014 inch) is inserted into the guiding catheter so as to allow the guide wire to pass through the stricture portion of the coronary artery. Then, a balloon catheter equipped with a balloon at the distal end is inserted along the guide wire, and the balloon is expanded so as to expand the stricture portion, followed by withdrawing the balloon catheter. Further, a contrast medium is injected through the guiding catheter so as to confirm the state of expansion of the stricture portion. If the stricture portion is sufficiently expanded and if there is no inconvenience, the manual operation is finished. If the expansion is insufficient or the inner membrane is peeled off, the operation to retain the stent is carried out as follows.

Specifically, the stent is mounted on the balloon, which is in the folded state, of a balloon catheter, and the balloon catheter is moved along the guide wire to the stricture portion as described above such that the distal end of the balloon catheter is positioned within the stricture portion. Under this condition, the position of the distal end of the balloon catheter is confirmed by an X-ray observation. Then, a contrast medium is injected into the balloon under a high pressure so as to expand the balloon. By the expansion of the balloon, the stent is plastically deformed such that the diameter of the stent is increased in the radial direction so as to be expanded (swollen) as shown in FIG. 3 or 6, thereby expanding the stricture portion. Then, the pressure of the balloon is removed so as to shrink the balloon. In this case, the stent is not shrunk and is retained in its position because the stent has an expansion holding force (shape holding force) derived from the plastic deformation so as to maintain the expanded state of the blood vessel and, thus, to improve the blood flow disorder. It should be noted in this connection that, in the stent according to the second embodiment of the present invention, which is shown in FIG. 4, the expanding member is formed of the waved element that is arranged in a spiral fashion and the connecting element, which are each arranged in a continuous fashion. It follows that the expanded state can be maintained with substantially uniform expanding force relative to the blood vessel. In addition, even in a bent stricture portion, the stent can be bent more easily along the bending of the bent stricture portion.

The present invention will now be described in more detail with reference to the Examples of the present invention given below.

Example 1

A long stainless steel pipe (SUS316L) having a diameter of 1.4 mm and a wall thickness of 0.10 mm was cut into a pipe piece having a length of 100 mm. A desired stent was manufactured by a laser processing method from the cut piece of the stainless steel pipe. SL116E (trade name of a YAG laser manufactured by NEC Corporation) was used as the laser processing machine. Specifically, the cut piece of the stainless steel pipe was set on a tool equipped with a rotary motor provided with a chuck mechanism so as to prevent the axis of the metal pipe piece from being shifted, and the tool was set on an XY table capable of a numerical control. The XY table and the rotary motor were connected to a personal computer, and the output of the personal computer was set to be supplied to the numerical controller of the XY table and to the rotary motor. Drawing software was stored in the personal computer, and the developed drawing of the stent constructed as shown in FIG. 1 was supplied to the personal computer. Then, the XY table and the rotary motor were driven on the basis of the drawing data generated from the personal computer, followed by irradiating the stainless steel pipe piece that was moved in accordance with the driving of the XY table and the rotary motor with a laser beam so as to prepare the stent structure shaped as shown in FIG. 1. Incidentally, a core was inserted into the pipe piece so as to prevent the laser beam from penetrating through the pipe piece. The laser processing was carried out under a current value of 25 A, an output of 1.5 W and a driving speed of 10 mm/sec.

As a result, a stent was prepared shaped as shown in FIG. 1. The stent thus prepared had an entire length of 15 mm and an outer diameter of 1.4 mm. Also, the waved element constituting the expanding member had a width of 0.11 mm and the connecting member had a width of 0.05 mm. When the stent was mounted on a delivery balloon, the outer diameter of the stent was decreased to about 1.0 mm. The width of the ridge and the bottom of the waved element was 0.36 mm, and the height of the largest wave of the connecting member was 0.50 mm, which was larger than the width of the ridge and the bottom of the waved element. Also, the distance between the adjacent expanding members was 0.51 mm, and the total length of each of the connecting members was 2.13 mm. Further, the linear distance between the ridges or between the bottoms of the adjacent expanding elements was 1.55 mm.

The clearance 21 of the stent described previously had a circumferential length of 6.35 mm, which corresponds to 2.02 mm of the diameter of a circle. On the other hand, if the adjacent ridges are assumed to be joined to each other by a straight joining member, the circumferential length of the clearance of the stent formed in this case is 4.80 mm, which corresponds to 1.53 mm of the diameter of a circle. It follows that, if the stent of the present invention is used, it is possible to use a balloon of 2.0 mm for a branched blood vessel. However, where the connecting member is straight, it is possible to use only a balloon of 1.5 mm. In terms of the cross-sectional area, the diameter of 2.0 mm is 1.7 times as much as the diameter of 1.5 mm and, thus, is advantageous in this respect. It is considered reasonable to understand that, since the waved connecting member has a small width, the stent can be deformed easily along the balloon when the balloon is expanded so as to contribute to the merit described above.

Example 2

A long stainless steel pipe (SUS316L) having a diameter of 1.4 mm and a wall thickness of 0.10 mm was cut into a pipe piece having a length of 100 mm. A desired stent was manufactured by a laser processing method from the cut piece of the stainless steel pipe. SL116E (trade name of a YAG laser manufactured by NEC Corporation) was used as the laser processing machine. Specifically, the cut piece of the stainless steel pipe was set on a tool equipped with a rotary motor provided with a chuck mechanism so as to prevent the axis of the metal pipe piece from being shifted, and the tool was set on an XY table capable of a numerical control. The XY table and the rotary motor were connected to a personal computer, and the output of the personal computer was set to be supplied to the numerical controller of the XY table and to the rotary motor. Drawing software was stored in the personal computer, and the developed drawing of the stent constructed as shown in FIG. 4 was supplied to the personal computer. Then, the XY table and the rotary motor were driven on the basis of the drawing data generated from the personal computer, followed by irradiating the stainless steel pipe piece that was moved in accordance with the driving of the XY table and the rotary motor with a laser beam so as to prepare the stent structure shaped as shown in FIG. 4. The laser processing was carried out under a current value of 25 A, an output of 1.5 W and a driving speed of 10 mm/sec.

As a result, a stent was prepared shaped as shown in FIG. 4. The stent thus prepared had an entire length of 15 mm and an outer diameter of 1.4 mm. Also, the waved element constituting the expanding member had a width of 0.11 mm and the connecting member had a width of 0.05 mm. When the stent was mounted on a delivery balloon, the outer diameter of the stent was decreased to about 1.0 mm. The width of the ridge and the bottom of the waved element was 0.36 mm, and the height of the largest wave of the connecting member was 0.50 mm, which was larger than the width of the ridge and the bottom of the waved element. Also, the long linear segment of the waved element had a length of 1.69 mm, and the short segment had a length of 1.29 mm. Further, the distance between the adjacent waves was 0.76 mm, and the total length of each of the connecting members was 4.75 mm. Still further, the linear distance between the ridges or between the bottoms of the adjacent waved elements was 2.3 mm.

The clearance 41 of the stent described previously had a circumferential length of 10.34 mm, which corresponds to about 3.3 mm of the diameter of a circle. On the other hand, if the adjacent ridges are assumed to be joined to each other by a straight joining member, the circumferential length of the clearance of the stent formed in this case is 7.56 mm, which corresponds to 2.4 mm of the diameter of a circle. It follows that, if the stent of the present invention is used, it is possible to use a balloon of 3.25 mm for a branched blood vessel. However, where the connecting member is straight, it is possible to use only a balloon of 2.25 mm. In terms of the cross-sectional area, the diameter of 3.25 mm is 2.28 times as much as the diameter of 2.25 mm and, thus, is advantageous in this respect. It is considered reasonable to understand that, since the waved connecting member has a small width, the stent can be deformed easily along the balloon when the balloon is expanded so as to contribute to the merit described above.

As described above, a stent according to the present invention is excellent in its flexibility in the axial direction either before or after expansion. It follows that, when a stent of the present invention is delivered, it is possible to deliver the stent even through a difficult diseased portion which is bent and calcified. Also, since the stent has a flexibility such that, even when retained in a bent diseased portion, the stent can be bent easily, it can be expected that re-stricture can be prevented at the edge of the stent. Further, a stent of the present invention is provided with a waved connecting member having a plurality of waves, and the total length of the waved portion is longer than the straight portion, leading to the merit that a large balloon can be applied to a branched blood vessel.

Additional advantages and modifications will readily occur to those skilled in the art. Therefore, the present invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stent formed to be tubular as a whole, having a first outer diameter capable of insertion into a tubular lumen of a living body, and capable of expansion to have a second outer diameter larger than said first outer diameter when an expanding force directed outward in a radial direction is imparted within the stent, comprising a plurality of annular expanding members arranged a predetermined distance apart from each other in an axial direction of the stent and each formed of a waved element, each of the waved elements comprising an alternating arrangement of ridges and bottoms so that each ridge is circumferentially followed by one of the bottoms; and a plurality of waved connecting members connecting each of a plurality of the ridges of axially adjacent wave elements to one another and connecting each of a plurality of the bottoms of axially adjacent wave elements to one another; wherein said plurality of annular expanding members are arranged in an axial direction of the stent such that no substantial phase difference exists in the waves of the waved elements, and each of the waved connecting members has a plurality of waves including a wave formed in a clearance between adjacent annular expanding members and having an amplitude larger than that of the other wave, the largest wave included in each of said waved connecting members having a wave height measured circumferentially of the stent, the ridge or bottom of the waved elements having a width measured circumferentially of the stent, the wave height of the largest wave included in each of said waved connecting members being larger than the width of the ridge or bottom of the waved element under the state that the stent possesses said first outer diameter;

wherein the plurality of waves comprising each waved connecting member includes a plurality of waves positioned between portions of a single one of the waved elements.

2. The stent according to claim 1, wherein each of the ridges of each waved element is connected to one of the ridges in the axially adjacent waved element by one of the waved connecting members, and each of the bottoms of each waved element is connected to one of the bottoms in the axially adjacent waved element by one of the waved connecting members.

3. The stent according to claim 1, wherein each of said waved connecting members possesses a width not larger than ½ of the width of the waved element.

4. The stent according to claim 3, wherein the width of each of said waved connecting members falls within a range of between 0.03 mm and 0.08 mm.

5. The stent according to claim 1, wherein said waved connecting member possesses a total length at least 1.3 times as much as a straight distance between the ridges or between the bottoms of the waved elements of the adjacent annular expanding members.

6. The stent according to claim 1, wherein the clearance between adjacent annular expanding members possesses a width falling within a range of between 0.4 mm and 0.8 mm.

7. The stent according to claim 1, wherein at least some of the waved connecting members have at least three waves.

8. The stent according to claim 1, wherein each of the waved elements comprises a plurality of linear segments, and each of the waved connecting members comprises first and second waves positioned in a clearance between adjacent linear segments and a third wave not positioned between the adjacent linear segments, the third wave being positioned between axially adjacent annular expanding members, the third wave possessing an amplitude larger than that of the first and second waves.

9. A stent formed to be tubular as a whole, having a first outer diameter capable of insertion into a tubular lumen of a living body, and capable of expansion to have a second outer diameter larger than said first outer diameter upon radial outward expansion of the stent, comprising a plurality of annular expanding members arranged a predetermined distance apart from each other in an axial direction of the stent and each formed of a waved element, each of the waved elements comprising an alternating arrangement of ridges and bottoms so that each ridge is circumferentially followed by one of the bottoms, the plurality of annular expanding members including a first annular expanding member and a second annular expanding member, the first annular expanding member being immediately adjacent the second annular expanding member in the axial direction of the stent; and a plurality of waved connecting members connecting each of a plurality of the ridges of the wave element of the first annular expanding member to a respective one of the ridges of the wave element of the second annular expanding member and connecting each of a plurality of the bottoms of the wave element of the first annular expanding member to a respective one of the bottoms of the wave element of the second annular expanding member; the waved element forming said first annular expanding member comprising a plurality of substantially linear segments, said first and second annular expanding members being arranged such that no substantial phase difference exists in waves of the waved elements forming the first and second annular expanding members, and each of the waved connecting members comprising a plurality of waves including a wave formed in a clearance between the first and second annular expanding members and having an amplitude larger than that of another wave of the waved connecting member, the largest wave included in each of said waved connecting members having a wave height measured circumferentially of the stent, the ridge or bottom of the waved elements having a width measured circumferentially of the stent, the wave height of the largest wave included in each of said waved connecting members being larger than the width of the ridge or bottom of the waved element under the state that the stent possesses said first outer diameter, the plurality of waves forming each of at least two of the waved connecting members including a plurality of waves positioned between the substantially linear segments of the first annular expanding member.

10. The stent according to claim 9, wherein each of the ridges of each waved element is connected to one of the ridges in the axially adjacent waved element by one of the waved connecting members, and each of the bottoms of each waved element is connected to one of the bottoms in the axially adjacent waved element by one of the waved connecting members.

11. The stent according to claim 9, wherein each of the ridges of the waved element of the first annular expanding member is connected to one of the ridges of the waved element of the second annular expanding member by one of the waved connecting members, and each of the bottoms of the waved element of the first annular expanding member is connected to one of the bottoms of the waved element of the second annular expanding member by one of the waved connecting members.

12. The stent according to claim 9, wherein each of said waved connecting members possesses a width not larger than ½ of the width of the waved element.

13. The stent according to claim 9, wherein each of said waved connecting members possesses a width falling within a range of between 0.4 mm and 0.8 mm.

14. The stent according to claim 9, wherein said waved connecting member possesses a total length at least 1.3 times as much as a straight distance between the ridges or between the bottoms of the waved elements of the first and second adjacent annular expanding members.

15. The stent according to claim 9, wherein the width of the clearance between adjacent annular expanding members falls within a range of between 0.4 mm and 0.8 mm.

16. The stent according to claim 9, wherein the plurality of annular expanding members also comprises a third annular expanding member immediately adjacent the second annular expanding member and spaced apart from the second annular expanding member in the axial direction of the stent, the third annular expanding member being formed of a waved element including a plurality of substantially linear segments, and a plurality of waved connecting members connecting ridges and/or bottoms of the waved elements of the second and third annular expanding members; a portion of the wave of at least two of the plurality of waved connecting members which connect the second and third annular expanding members being positioned between two of the substantially linear segments of the third annular expanding member.

17. The stent according to claim 9, wherein the waved element forming said second annular expanding member comprises a plurality of substantially linear segments, the plurality of annular expanding members comprising a third annular expanding member immediately adjacent the second annular expanding member and spaced apart from the second annular expanding member in the axial direction of the stent, the third annular expanding member being formed of a waved element which includes a plurality of substantially linear segments, and a plurality of waved connecting members connecting ridges and/or bottoms of the waved elements of the second and third annular expanding members; a portion of the wave of several of the plurality of waved connecting members which connect the second and third annular expanding members being positioned between two of the substantially linear segments of the second annular expanding member, and a portion of the wave of several of the plurality of waved connecting members which connect the second and third annular expanding members being positioned between two of the substantially linear segments of the third annular expanding member.

18. The stent according to claim 9, wherein each of the waved elements comprises a plurality of linear segments, and wherein each of the annular expanding members is connected to an adjacent annular expanding member by a plurality of the waved connecting members so that each ridge of each annular expanding member is connected to one of the ridges of the axially adjacent annular expanding member by one of the waved connecting members and so that each bottom of each annular expanding member is connected to one of the bottoms of the axially adjacent annular expanding member by one of the waved connecting members, each waved connecting member comprising first and second waves positioned in a clearance between adjacent linear segments and a third wave not positioned between the adjacent linear segments, the third wave being positioned between axially adjacent annular expanding members, the third wave possessing an amplitude larger than that of the first and second waves.

19. A stent formed to be tubular as a whole, having a first outer diameter capable of insertion into a tubular lumen of a living body, and capable of expansion to have a second outer diameter larger than said first outer diameter upon radial outward expansion of the stent, comprising a plurality of annular expanding members arranged a predetermined distance apart from each other in an axial direction of the stent and each formed of a waved element, each of the waved elements comprising an alternating arrangement of ridges and bottoms so that each ridge is circumferentially followed by one of the bottoms, the plurality of annular expanding members including a first annular expanding member and a second annular expanding member, the first annular expanding member being immediately adjacent the second annular expanding member in the axial direction of the stent; and a plurality of waved connecting members connecting each of a plurality of the ridges of the wave element of the first annular expanding member to a respective one of the ridges of the wave element of the second annular expanding member and connecting each of a plurality of the bottoms of the wave element of the first annular expanding member to a respective one of the bottoms of the wave element of the second annular expanding member; the waved element forming said first annular expanding member and the waved element forming said second annular expanding member comprising a plurality of substantially linear segments, said first and second annular expanding members being arranged such that no substantial phase difference exists in waves of the waved elements forming the first and second annular expanding members, and each of the waved connecting members comprising a plurality of waves including a wave formed in a clearance between the first and second annular expanding members and having an amplitude larger than that of another wave of the waved connecting member, the largest wave included in each of said waved connecting members having a wave height measured circumferentially of the stent, the ridge or bottom of the waved elements having a width measured circumferentially of the stent, the wave height of the largest wave included in each of said waved connecting members being larger than the width of the ridge or bottom of the waved element under the state that the stent possesses said first outer diameter, a portion of the wave of at least two of the plurality of waved connecting members being positioned between the substantially linear segments of the first annular expanding member, and the plurality of waves forming each of at least two of the waved connecting members including a plurality of waves positioned between the substantially linear segments of the second annular expanding member.

20. The stent according to claim 19, wherein each of the ridges of each waved element is connected to one of the ridges in the axially adjacent waved element by one of the waved connecting members, and each of the bottoms of each waved element is connected to one of the bottoms in the axially adjacent waved element by one of the waved connecting members.

21. The stent according to claim 19, wherein each of the ridges of the waved element of the first annular expanding member is connected to one of the ridges of the waved element of the second annular expanding member by one of the waved connecting members, and each of the bottoms of the waved element of the first annular expanding member is connected to one of the bottoms of the waved element of the second annular expanding member by one of the waved connecting members.

22. The stent according to claim 19, wherein each of said waved connecting members possesses a width not larger than ½ of the width of the waved element.

23. The stent according to claim 19, wherein each of said waved connecting members possesses a width falling within a range of between 0.4 mm and 0.8 mm.

24. The stent according to claim 19, wherein each of the waved elements comprises a plurality of linear segments, and wherein each of the annular expanding members is connected to an adjacent annular expanding member by a plurality of the waved connecting members so that each ridge of each annular expanding member is connected to one of the ridges of the axially adjacent annular expanding member by one of the waved connecting members and so that each bottom of each annular expanding member is connected to one of the bottoms of the axially adjacent annular expanding member by one of the waved connecting members, each waved connecting member comprising first and second waves positioned in a clearance between adjacent linear segments and a third wave not positioned between the adjacent linear segments, the third wave being positioned between axially adjacent annular expanding members, the third wave possessing an amplitude larger than that of the first and second waves.

* * * * *